(12) United States Patent
Suthanthiran et al.

(10) Patent No.: US 8,170,647 B2
(45) Date of Patent: May 1, 2012

(54) FIDUCIARY MARKERS AND METHOD OF USE THEREOF

(75) Inventors: Krishnan Suthanthiran, Springfield, VA (US); Rashmi Amin, Fairfax, VA (US)

(73) Assignee: Best Medical International, Inc, Springfield, VA (US)

( * ) Notice: Subject to any disclaimer, the term of this patent is extended or adjusted under 35 U.S.C. 154(b) by 1456 days.

(21) Appl. No.: 11/423,906

(22) Filed: Jun. 13, 2006

(65) Prior Publication Data

US 2007/0238983 A1    Oct. 11, 2007

Related U.S. Application Data

(60) Provisional application No. 60/760,388, filed on Jan. 20, 2006.

(51) Int. Cl.
 *A61B 6/00* (2006.01)
(52) U.S. Cl. .................................................... 600/431
(58) Field of Classification Search .............. 600/3, 7, 600/8, 407–437, 439, 458; 606/912
See application file for complete search history.

(56) References Cited

U.S. PATENT DOCUMENTS

| | | | | |
|---|---|---|---|---|
| 5,394,457 A * | 2/1995 | Leibinger et al. | ............. | 378/162 |
| 5,397,329 A * | 3/1995 | Allen | ............. | 378/205 |
| 5,636,255 A * | 6/1997 | Ellis | ............. | 378/20 |
| 6,173,715 B1 * | 1/2001 | Sinanan et al. | ............. | 128/899 |
| 6,632,176 B2 * | 10/2003 | McIntire et al. | ............. | 600/439 |
| 6,716,156 B2 * | 4/2004 | Menuhr et al. | ............. | 600/8 |
| 6,725,083 B1 * | 4/2004 | Burbank et al. | ............. | 600/431 |
| 6,993,375 B2 * | 1/2006 | Burbank et al. | ............. | 600/431 |
| 7,280,865 B2 * | 10/2007 | Adler | ............. | 600/429 |
| 7,736,293 B2 * | 6/2010 | Lamoureux et al. | ............. | 600/8 |
| 7,776,310 B2 * | 8/2010 | Kaplan | ............. | 424/1.25 |
| 2004/0019265 A1 * | 1/2004 | Mazzocchi et al. | ............. | 600/407 |

* cited by examiner

*Primary Examiner* — Francis Jaworski
(74) *Attorney, Agent, or Firm* — Best Medical International; O'Neal R. Mistry

(57) ABSTRACT

The invention provides devices and methods used to locate target areas within a patient for repeat therapeutic treatments. In the invention, fiduciary markers made of metal or metal alloys are placed within a patient near or at a target site as reference coordinates for particular body locations on the patient. Repeat treatments may then be given to the patient over a period of time based on the coordinates given by the fiduciary markers. The fiduciary markers are specially shaped or put into strand to improve marker attachment and prevent marker migration.

23 Claims, 3 Drawing Sheets

FIDUCIARY MARKERS AND METHOD OF USE THEREOF

CROSS-REFERENCE TO RELATED APPLICATIONS

The present application is related to a provisional application, titled FIDUCIARY MARKERS AND METHOD OF USE THEREOF, application Ser. No. 60/760,388, filed on Jan. 20, 2006 by inventor Krishnan Suthanthiran and Rashimi Amin. All of this application is incorporated herein by reference.

BACKGROUND

The accurate positioning of patients and tissue localization are crucial steps before performing many types of medical treatments. One category of medical treatments in which the proper placement and verification of the position of patient or tissue is of particular importance is in the field of radiation therapy.

Radiation therapy involves medical procedures that selectively expose certain areas of a human body, such as cancerous tumors, to high doses of radiation. The intent of the radiation therapy is to irradiate the targeted biological tissue such that the harmful tissue is destroyed. To minimize damage to surrounding body tissue, many conventional treatment methods utilize "dose fractionating" technique. According to "dose fractionating" technique, radiation dosage is delivered in a planned series of treatment sessions with each delivers only a portion of the total planned dosage. Healthy body tissue typically has greater capacity to recover from the damage, thus reducing the amount of permanent damage to healthy tissue while maintaining enough radiation exposure to destroy tumoral tissue.

The efficacy of "dose fractionating" procedure depends in large part upon the ability to irradiate the exact same position on a body over multiple radiation sessions. The goal is to place the patient or body parts of the patient in a way that the target area is in the same position relative to the radiation source in each and every treatment session. Inaccuracies in positioning could result in errors in radiation dosage and treatment locations, leading to unpredictable disease relapse or damage to healthy tissues. However, problem arises when doctors attempting to recreate the same target area of a patient at every radiation session.

The traditional approach to control patient positioning is to place marks or tattoos at specific locations on the patient's skin. Several laser or light sources from predetermined locations project beams of light at the patient's body. To control the patient positioning, a therapist moves the patient until the marks are aligned with the lines from the lasers or light sources. A significant drawback to this approach is that the accuracy and consistency of the patient positioning is heavily dependent upon the skill level of the therapist in manually positioning the patient. In addition, with heavier patients, it is possible that only the skin of the patient is moved into the proper position without moving the body part to be irradiated into the appropriate position. Moreover, this approach does not provide an efficient way to record and reflect the positioning quality in the patient's records. Shortcoming of this approach may be fully illustrated by problems faced in external-beam radiotherapy (EBRT). EBRT is a commonly used curative treatment for a variety of cancers including prostate cancer. The efficacy and tolerance of EBRT depends on accurate localization and the maximal exclusion of critical normal structures, such as organs at risk, with conformal field arrangements. However, the position of the target is typically inferred only from skin markings, which serves as external references points, which are used to align the patients on the treatment machine. The accuracy of this alignment is monitored with periodic portal imaging of the skeletal structures of the lower pelvis. Although external reference points should be reproducibly related to skeletal structures, portal imaging often reveals displacement from the intended position, and this is often referred to as setup variation. In prostate cancer EBRT, investigators demonstrated that the error in field alignment might exceed 10 mm along each of the mutually perpendicular axes of the coordinate system. Vigneault E, Pouliot J, Laverdiere J, et al. Electronic portal imaging device detection of radio-opaque markers for the evaluation of prostate position during megavoltage irradiation. *Int J Radiat Oncol Biol Phys* 1997; 37:205-212. Tinger A, Michalski J M, Cheng A, et al. A critical evaluation of the planning target volume for 3-D conformal radiotherapy of prostate cancer. *Int J Radiat Oncol Biol Phys* 1998; 42:213-221. Stryker J A, Shafer J, Beatty R E. Assessment of accuracy of daily set-ups in prostate radiotherapy using electronic imaging. *Br J Riol* 1999; 72:579-583. Zelefsky M J, Crean D, Mageras G S, et al. Quantification and predictors of prostate position variability in 50 patients evaluated with multiple CT scans during conformal radiotherapy. *Radiother Oncol* 1999; 50:225-234. The setup variation only partially accounts for uncertainties in the position of the target relative to the treatment beam. The position of the prostate is not fixed relative to the skin marks or the skeletal anatomy of the pelvis. The state of bladder and rectal filling may result in displacement of the prostate. Roeske J C, Forman J D, Mesina C F, et al. Evaluation of changes in the size and location of the prostate, seminal vesicles, bladder, and rectum during a course of external beam radiation therapy. *Int J Radiat Oncol Biol Phys* 1995; 37:205-212. Beard C J, Kijewshi P, Bussiere M, et al. Analysis of prostate and seminal vesicle motion: Implications for treatment planning. *Int J Radiat Oncol Biol Phys* 1996; 34:451-458. This organ motion adds an additional component of uncertainty, which may also exceed 10 mm, in localizing the target for treatment delivery.

Another approach to control patient positioning is to utilize an immobilization device to maneuver the patient into a particular position. An immobilization device physically attaches to the human body to keep the patient from moving once proper positioning is achieved. A drawback of using an immobilization device is that such devices do not exist for all body parts. Immobilization devices are generally effective only for positioning the head and neck of a patient. Moreover, in many known immobilization devices, a patient can still move to a significant degree within the confines of the immobilization device. In addition, these devices can be extremely uncomfortable for the patient. Furthermore, the immobilization has little or no control over aforementioned organ movement.

To solve these problems, researchers have developed a real-time electronic portal imaging device procedure to identify gold markers located within the patient's body and correct daily variations in target position during external beam radiotherapy for prostate cancer. Gold intraprostatic markers are implanted around the target of interest in the patients through CT-guided transgluteal approach or a transscrectal ultrasound-guided perineal approach and are used to localize internal reference points. The researchers found that a direct match to the markers provides an easy, time-efficient, and more reliable method than using portal skeletal images and obviates the need to calculate the centroid. M. G. Herman, T. M. Pisansky, J. J. Kruse, et al., Technical aspects of daily online positioning of the prostate for three-dimensional conformal radiotherapy using an electronic portal-imaging device, *Int. J. of Radiation Oncology Biol. Phys.*, 57:4, pp 1131-1140 (2003). J. M. Schallenkamp, M. G. Herman, J. Kruse, T. M. Pisansky, Prostate position relative to pelvic bony anatomy based on intraprostatic gold markers and electronic portal images, *Int. J. of Radiation Oncology Biol. Phys.*, accepted for publication Feb. 17, 2005. However, because the markers used in these experiments are designed for other purposes and are mostly cylindrical in shape with smooth surfaces, the same study also revealed that the fiduciary markers might change positions over time.

Thus, there is a need for better designed markers and method that improve attachment markers to the target sites within a patient and thus minimizes marker migration after implant.

SUMMARY

The invention provides devices and methods for locating a target tissue within a patient and for positioning a patient for medical treatment procedures, such as three-dimensional conformal radiotherapy. According to an aspect of the invention, markers are placed within a patient, as reference coordinates for particular body locations on the patient. The markers may be shaped to provide firm attachment to the body, which allows easy and accurate patient positioning and tissue locating for a sequential treatments. An embodiment of a device having features of this invention may be dumbbell shaped marker with a spherical end and a conic end. The conic end of the fiduciary marker may have a series of grooves cut into it creating a rougher surface to enhance marker attachment. Another embodiment of a device having features of the invention is cylindrical marker with flexible fingers on one of its end. The closed fingers may open up once placed with the patient. Yet another embodiment of a device having features of the invention is markers enclosed in absorbable strand or wrapped in sutures to form longer fiduciary marker stands of desired lengths. In addition, the marker body shape may have one or more distinct features, which may be visualized in different marker orientations.

DESCRIPTION OF THE FIGURES

The accompanying drawings, which are incorporated in and form a part of the specification, illustrate embodiments of the present invention and, together with the description, serve to explain the principles of the invention. Because the figures are provided for the sole purpose of illustration, they are not drawn to proportions.

DETAILED DESCRIPTION OF THE INVENTION

The drawings are shown for purposes of illustration. The invention is embodied in a fiduciary marker or a fiduciary marker strand. In the preferred embodiments of the present invention, the marker is used in the human body. However, it will be recognized that further embodiments of the invention may be used in animals or other applications where positioning a body or body parts are required. The invention is also not limited to radiotherapy. The present invention provides devices and methods used to locate target tissue in a patient for sequential treatments.

Figure 1A:
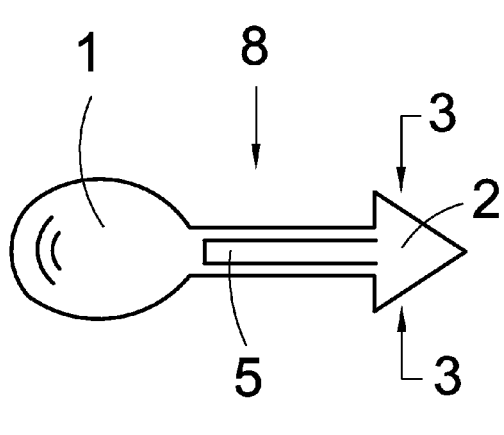
FIG. 1A is a perspective view of a device embodying features of the invention.
Figure 1B:
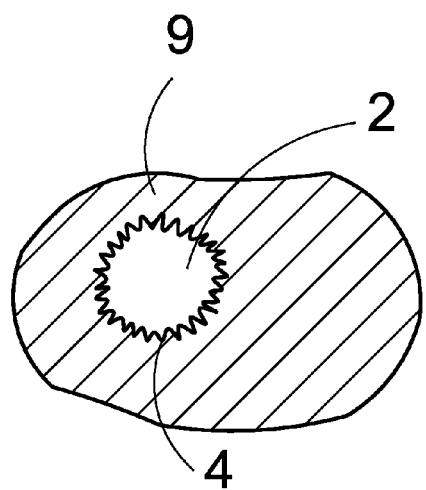
FIG. 1B is a cross-sectional view of one embodiment of cone-end of the device along 3-3 of FIG. 1A.

Referring to FIG. 1A, a fiduciary marker in accordance with an embodiment of the present invention includes a dumbbell shaped radio-opaque seed 8 with a spherical end 1 and a cone end 2 connected by a cylindrical middle section 5. The cone shaped end of the marker (radio-opaque seed) may allow easier and deeper insertion into the tissue adjacent or on a target site. Once placed within a patient, the shape of the conic end may impede detachment of the marker (radio-opaque seed) from the body tissue and prevent marker migration within the body. The shape of the marker (radio-opaque seed) may also indicate the direction of the marker, which can be used to further marking the tissue or organ. A series of grooves 4 may be cut into the surface of the cone shaped end of a marker (radio-opaque seed) 2. FIG. 1B shows a cross-sectional view of the fiduciary marker (radio-opaque seed) of FIG. 1A. These grooves 4 may increase surface roughness of the end and increase frictions between the surfaces 3 of the fiduciary marker and the tissue 9 within which the marker is embedded. This feature allows the marker (radio-opaque seed) 2 to take even a stronger hold of the tissue.

Figure 2A:
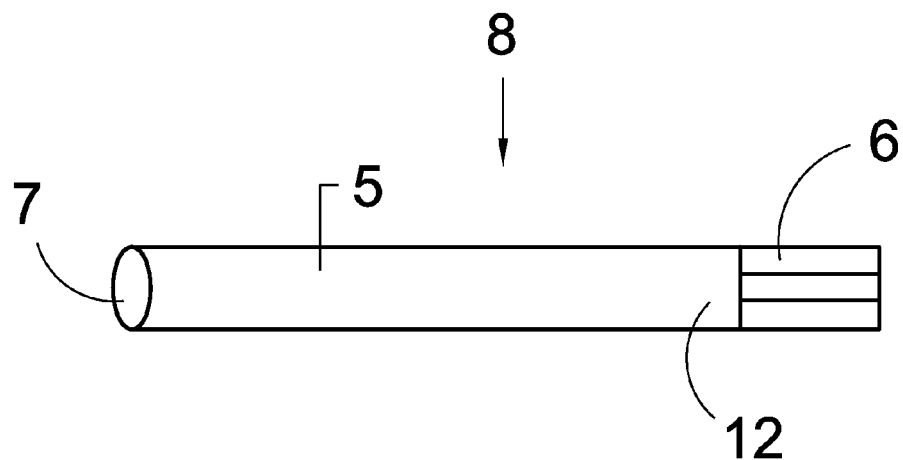
FIG. 2A is another perspective view of a device embodying features of the invention.
Figure 2B:
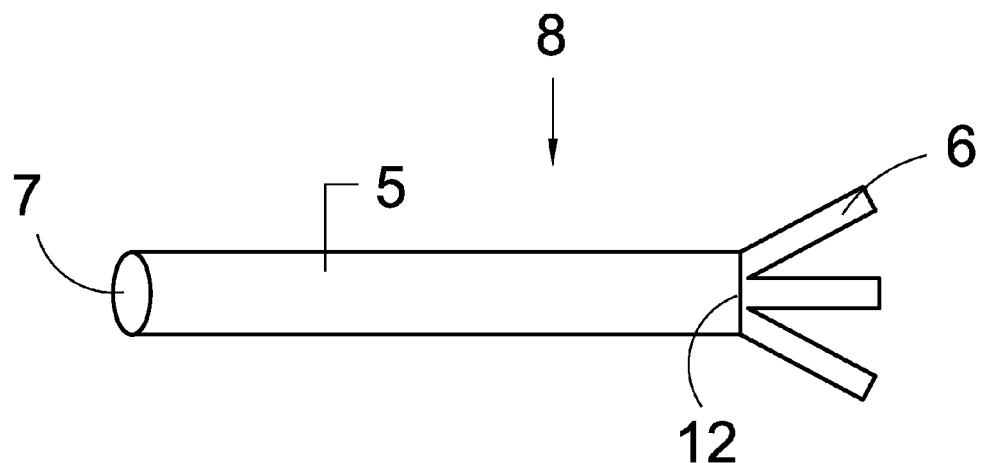
FIG. 2B is another aspect of the device shown in FIG. 2A.

FIG. 2A illustrates another embodiment of a fiduciary marker having features of the invention. The fiduciary marker 8 may be a uniform cylinder with a proximal end 7 and a distal end 12. Cross section 5 of the fiduciary marker 8 may be of any shape, such as round, square, rectangular or pentagon. The distal end 12 of the fiduciary marker 8 may have one or more fingers or forks 6. The fingers or forks 6 may be held together before implantation, for example by a needle or a catheter and may open up after placement within the targeted tissue of a patient. The opened forks 6 of the fiduciary marker 8, as shown in FIG. 2B may be extended into tissue surrounding or at a target site, and prevent marker migration over time. The end of the fingers or forks may be sharpened to allow easy insertion.

Figure 3:
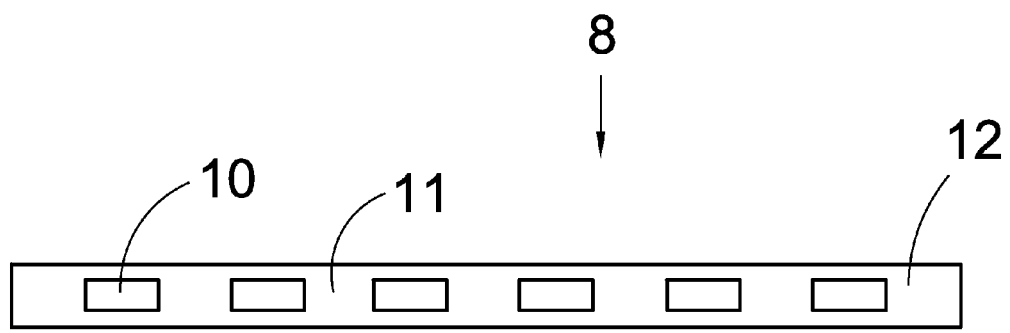
FIG. 3 is a cross-sectional view of a device embodying features of the invention along.

FIG. 3 shows yet another embodiment of the fiduciary makers having features of the invention. In this embodiment, radio-opaque markers or strands are used to mark soft tissue, for therapeutic procedures. As shown in FIG. 3, a marker strand 8 may comprise of one or more radio-opaque seeds 10 separated by several absorbable spacers 11 and enclosed by an absorbable strand 12. In the alternative, fiduciary markers may be coated with absorbable materials and formed into a strand. The increased length of the fiduciary marker strand may greatly reduce markers migration after implantation, relative to the target site or to each other. Therefore, a fiduciary marker strand may provide more efficient and reliable internal reference points for future treatments. The total length of the strand may be around 1-30 centimeters depending on the tissue characteristics. The absorbable strands, spacers or coating may be such that it will degrade in vivo over time. Such coatings may be selected from polymers such as polydextrans, polyvinylpyrrolidone, poly(bis(p-carboxyphenoxy)-propane), lactide, and copolymers derived thereof, and biopolymers such as gelatin, human serum, albumin, cellulose, etc. CP medical, Inc of Portland, Oreg., is a manufacturer of a type of FDA 501(K) approved absorbable strands.

In yet another embodiment, the fiduciary markers are embedded or wrapped in sutures. Recently clinical data at Wake Forest University have shown that patients who were treated with radioactive seeds embedded in suture have significantly improved dosimetric coverage of the prostate gland than those who were implanted with loose seeds. William Robert Lee, et al., *Radiotherapy and Oncology* 2002, 65:123-127. Baird, et al., also observed that placing two markers separated by absorbable spacers or sutures prior to prostate brachytherapy may help reduce marker migration and improve dosimetric result. Baird M C, Holt R W, Selby T L, Improvement of trasperineal implant dosimetry by intraoperative cystoscopic confin of prostate anatomy. *J Urol* 2000; 164:406-410.

In all embodiments, the fiduciary markers may be made of stainless steel, gold, titanium, platinum, tantalum, copper, tungsten or other biocompatible metals or an alloy of metals. The length of a radio-opaque seed may range from 0.1 mm to 5 cm. The technology of making metal markers or seeds is well known in the art. One manufacturer having particular expertise in such manufacturing is BEST Medical International, Inc., in Springfield Va., which has been manufacturing and distributing medical devices and radioisotopes since 1977.

A method having features of the invention comprises the step of producing a fiduciary marker or a fiduciary marker strand having features of the invention. The fiduciary markers or strands may be then delivered by any method known to one of ordinary skill in the art. For example, the marker or marker strand may be implanted or inserted via use of an implantation gun, catheter, syringe or the like. It is preferable that the delivery of the fiduciary marker or marker strand include visual confirmation of its placement by common imaging modalities such as stereotaxy, ultrasound, CT or MRI. The specific placement pattern and quantity of fiduciary marker or marker strands may be selected depending on the anatomical and physiological properties of the area being treated, as known to one of ordinary skill in the art. The target sites on a patient may be then treated over a period of time based on coordinates given by the fiduciary markers. The method may further include a step where after several sessions of treatments, fiduciary markers are removed from the patient surgically with the assistance of stereotaxy, ultrasound, CT or MRI.

What is claimed is:

1. A marker for locating a plurality of regions of interest within the human anatomy in a subject comprising of at least one or more radio-opaque seeds,
   a. wherein said one or more radio-opaque seeds remain readily detectable in vivo using common imaging modalities;
   b. wherein said one or more radio-opaque seeds has a proximal end and a distal end, said one or more radio-opaque seeds further comprising,
      i. said distal end of said one or more radio-opaque seeds is shaped as a cone, wherein said cone comprises a series of grooves on the surface of said cone,
      ii. said proximal end of said one or more radio-opaque seeds is shaped as a ball, and
      iii. said proximal end and distal end is connected by a substantial cylindrical portion, wherein said cone is larger then said substantial cylindrical portion; and
   c. said marker being sized and shaped for firm implantation into tissue or organ of said subject.

2. A marker of claim 1 for locating a plurality of regions of interest within the human anatomy in a subject, wherein said one or more radio-opaque seeds haves a length ranging from 0.1 mm to 5 cm.

3. A marker of claim 1 for locating a plurality of regions of interest within the human anatomy in a subject, wherein said radio-opaque seed is made of a biocompatible metal or alloy of metals.

4. A marker of claim 1 for locating a plurality of regions of interest within the human anatomy in a subject, wherein said one or more radio-opaque seeds are made of a metal or metal alloy comprising as least one metal or metal alloy selected from the group consisting of stainless steel, gold, titanium, platinum, tantalum, copper, and tungsten.

5. A marker of claim 1 for locating a plurality of regions of interest within the human anatomy in a subject, wherein said one or more radio-opaque seeds are made of titanium.

6. A marker of claim 1 for locating a plurality of regions of interest within the human anatomy in a subject, wherein said one or more radio-opaque seeds can be of any size for said proximal end and said distal end.

7. A marker of claim 1 for locating a plurality of regions of interest within the human anatomy in a subject, wherein said one or more radio-opaque seeds further comprises:
   a plurality of fingers that is affixed to said distal end.

8. A marker of claim 7 for locating a plurality of regions of interest within the human anatomy in a subject, wherein said plurality of fingers
   remain closed before said one or more radio-opaque seeds are implanted into the subject; and
   said plurality of fingers open up when said one or more radio-opaque seeds are implanted into a desired tissue within the subject.

9. A marker of claim 1 for locating a plurality of regions of interest within the human anatomy in a subject, wherein said one or more said radio-opaque seeds are enclosed in an absorbable material forming substantially a strand,
   wherein said strand is comprises one or more radio-opaque seeds are separated by a plurality of absorbable spacers.

10. A marker of claim 9, wherein in the absorbable material is made of a polymer selected from a group consisting of
    a. a Polydextran;
    b. a Polyvinylpyrrolidone;
    c. a Poly(bis(p-carboxyphenoxy)-propane); or
    d. Biopolymer.

11. A marker of claim 9 for locating a plurality of regions of interest within the human anatomy in a subject, wherein at least two said radio-opaque seeds are separated by at least one absorbable spacer.

12. A marker of claim 11 for locating a plurality of regions of interest within the human anatomy in a subject, wherein at least one absorbable spacer is made of a polymer selected from a group consisting of
    a. a Polydextran;
    b. a Polyvinylpyrrolidone;
    c. a Poly(bis(p-carboxyphenoxy)-propane); or
    d. a Biopolymer.

13. A marker of claim 12 for locating a plurality of regions of interest within the human anatomy in a subject, wherein said biopolymer is selected from group consisting of gelatin, human scrum albumin, and cellulose.

14. A marker of claim 13, wherein at least two said radio-opaque seeds are wrapped in surgical suture to form said strand.

15. A marker of claim 14, wherein at least two said radio-opaque seeds are separated by at least one absorbable spacer.

16. A marker of claim 15, wherein said absorbable spacer is made of a polymer selected from a group consisting of
    a. a Polydextran;
    b. a Polyvinylpyrrolidone;
    c. a Poly(bis(p-carboxyphenoxy)-propane); or
    d. a Biopolymer.

17. A marker of claim 16, wherein said biopolymer is selected from group consisting of gelatin, human serum albumin, and cellulose.

18. A marker of claim 1 for locating a plurality of regions of interest within the human anatomy in a subject, wherein at least one said radio-opaque seed is wrapped, in surgical suture.

19. A marker of claim 1, wherein said radio-opaque seed has a length ranging from 01 mm to 5 cm.

20. A method of locating a region of interest in a subject for treatment using one or more markers, comprising the following steps:
   a. producing said one or more markers comprising of at least one radio-opaque seed wherein a seed remains readily detectable in vivo using common imaging modalities; and sized and shaped for firm implantation into tissue or organ of said subject;
   b. implanting said one or more, of markers into said tissue or organ close to or at said region of interest,
      i. wherein said implanting of said one or more markers into said tissue or organ further comprising a single needle containing at least two said one or more markers spaced a part with a determined distance to allow insertion of said one or more markers simulationally by only providing a single puncture point in a patient and said one or more markers contains a cone, a cylinder, and a 3-dimensional ball that contains a series of moves cut into the surface of said one or more markers;
   c. detecting said one or more markers in vivo using common imaging modalities;
   d. locating said region of interest using said one or more markers as reference points; and
   e. delivering treatment to the region of interest.

21. A method of claim 20, wherein said common imaging modalities includes:
   a. Stereotaxy;
   b. Ultrasound;
   c. CT; or
   d. MRI.

22. A method of claim 21, wherein said markers are implanted using one of the following a method:
   a. an implantation gun;
   b. a catheter; or
   c. a syringe.

23. A Method of claim 21, wherein said one or more markers
   a. are implanted for a period of time,
   b. are used for locating said region of interest over sequential treatments;
   c. are removed after said sequential treatments.

* * * * *